(12) United States Patent
Hyun et al.

(10) Patent No.: US 10,537,736 B2
(45) Date of Patent: Jan. 21, 2020

(54) SKIN CARE DEVICE

(71) Applicant: LG ELECTRONICS INC., Seoul (KR)

(72) Inventors: Seokjung Hyun, Seoul (KR); Gueisam Lim, Seoul (KR); Nayoung Kim, Seoul (KR); Dongwon Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 82 days.

(21) Appl. No.: 15/804,591

(22) Filed: Nov. 6, 2017

(65) Prior Publication Data

US 2018/0126160 A1 May 10, 2018

(30) Foreign Application Priority Data

Nov. 7, 2016 (KR) .................. 10-2016-0147445

(51) Int. Cl.
| | | |
|---|---|---|
| *A61N 1/36* | (2006.01) | |
| *A61B 5/00* | (2006.01) | |
| *A61N 1/04* | (2006.01) | |
| *A61B 5/01* | (2006.01) | |
| *A61B 5/053* | (2006.01) | |

(52) U.S. Cl.
CPC .......... *A61N 1/36031* (2017.08); *A61B 5/443* (2013.01); *A61B 5/4836* (2013.01); *A61N 1/0476* (2013.01); *A61B 5/01* (2013.01); *A61B 5/0537* (2013.01)

(58) Field of Classification Search
CPC .. A61N 1/36031; A61N 1/328; A61N 1/0476; A61N 1/322; A61H 23/02; A61B 5/4836; A61B 5/443; A61B 2562/029; A61B 2562/0209; A61B 2560/0425; A61B 5/0077; A61B 5/0537; A61B 5/01
See application file for complete search history.

(56) References Cited

U.S. PATENT DOCUMENTS

| | | | |
|---|---|---|---|
| 2006/0085056 A1* | 4/2006 | Schouenborg | ....... A61N 1/0456 607/148 |
| 2013/0282085 A1 | 10/2013 | Lischinsky et al. | |
| 2013/0289679 A1 | 10/2013 | Eckhouse et al. | |
| 2013/0333094 A1* | 12/2013 | Rogers | ..................... A61B 5/01 2/161.7 |

(Continued)

FOREIGN PATENT DOCUMENTS

| | | |
|---|---|---|
| KR | 10-1619858 B1 | 5/2016 |
| WO | 2012/144712 A1 | 10/2012 |
| WO | 2016/052893 A1 | 4/2016 |

*Primary Examiner* — Amanda K Hulbert
*Assistant Examiner* — Natasha Patel
(74) *Attorney, Agent, or Firm* — Dentons US LLP

(57) ABSTRACT

There is disclosed a skin care device comprising a main body configured to define an exterior; a tip head projected from the main body; a front cap configured to define a front surface of the tip head; a first electrode unit comprising a plurality of pin-electrodes aligned in a front surface of the front cap in an exposed array shape; a second electrode unit comprising positive electrodes and negative electrodes which are dividedly aligned in both sides of the first electrode unit; and a controller configured to control a high frequency voltage to be applied to the first electrode unit and the second electrode unit independently.

10 Claims, 11 Drawing Sheets

(56) References Cited

U.S. PATENT DOCUMENTS

| | | | |
|---|---|---|---|
| 2014/0207217 A1* | 7/2014 | Lischinsky | A61N 1/36014 607/102 |
| 2014/0288622 A1* | 9/2014 | Lee | A61N 1/0476 607/101 |
| 2015/0031964 A1* | 1/2015 | Bly | G16H 40/67 600/301 |
| 2017/0056685 A1* | 3/2017 | Harvey | A61N 5/0616 |
| 2017/0325566 A1* | 11/2017 | Franklin | A45D 26/0061 |

* cited by examiner

1

SKIN CARE DEVICE

CROSS-REFERENCE TO RELATED APPLICATIONS

This application claims priority to Korean Patent Application No. 10-2016-0147445 filed on Nov. 7, 2016 in Korea, the entire contents of which is hereby incorporated by reference in its entirety.

BACKGROUND OF THE DISCLOSURE

Field of the Disclosure

Embodiments of the present disclosure relate to a skin care device of which usability is enhanced.

Background of the Disclosure

Devices for skin care may be realized through diverse methods. When a micro stimulation is applied to the human skin, activity of cell is changed enough to bring an effect of skin tightening and whitening and the like.

As typical examples of the skin care methods, there are a non-invasive method configured to apply electrical stimulation to the skin and an invasive method configured to apply a physical stimulation.

A conventional skin care device is not a hand-carry type. As wireless communication has developed and internal components have been small-sized, many diverse portable skin care devices are commonly used.

The non-invasive stimulation method configured to apply an electrical stimulation for skin care may include a high frequency band type for applying a high frequency band electrical stimulation and an optical type for applying a visible ray area stimulation as main examples.

The high frequency band type skin care device may apply a 1 MHz high frequency stimulative energy to the human skin surface or the deep part of the skin.

However, the conventional skin care device is restricted only for deep skin care and it is not easy for a user to use a care for the skin surface and the deep part of the skin simultaneously or selectively.

To solve the disadvantage, the user is able to manage the skin by using a main device with diverse replaceable modules for various functions. However, no algorithm configured to automatically recognize the replaceable module is realized and the user has to set the module manually.

Meanwhile, the conventional skin care for business use is just small-sized and it is then insufficient to provide proper management for each user. For example, it is difficult to provide a corresponding feedback by recognizing a personal skin state. Even when there is a device capable of recognize the personal skin state, sensing accuracy can be deteriorated.

A new type of a skin care device is required which is capable of dataficating a personal skin state and skin care history and then providing a user's skin care based on the data.

SUMMARY OF THE DISCLOSURE

Accordingly, an object of the present invention is to address the above-noted and other problems and to solve the problem of failure in providing care for a skin surface and a deep skin part simultaneously or selectively.

Embodiments of the present disclosure may provide a skin care device comprising a main body configured to define an exterior; a tip head projected from the main body; a front cap configured to define a front surface of the tip head; a first electrode unit comprising a plurality of pin-electrodes aligned in a front surface of the front cap in an exposed array shape; a second electrode unit comprising positive electrodes and negative electrodes which are dividedly aligned in both sides of the first electrode unit; and a controller configured to control a high frequency voltage to be applied to the first electrode unit and the second electrode unit independently.

The first electrode unit array may be donut-shaped, and the positive electrodes and the negative electrodes of the second electrode unit may be divided in an inner area and an outer area of the donut shape, respectively.

The skin care device may further comprise a sensing unit provided in the tip head and configured to expose a sensor probe to a front surface of the front cap via the front cap.

The sensor probe may be provided in one area between positive electrodes and negative electrodes of the second electrode unit.

The sensor probe may be provided instead of one or more of the terminals provided in the array of the first electrode unit.

The sensing unit may comprise a temperature sensor configured to measure the skin temperature and a moisture sensor configured to measure the skin moisture, and the controller may be configured to determine whether to apply a voltage and differentiate the intervals and intensity of the applied voltage based on the temperature value measured by the temperature sensor and the moisture value measured by the moisture sensor.

The skin care device may further comprise a temperature sensor configured to measure the skin temperature; a memory in which temperature distribution data according to skin areas is stored; and a motion sensor configured to sense location or direction change, wherein the controller compares the skin temperature change according to the sensed location and direction change with the temperature distribution data and determines a relative location with the skin area based on the result of the comparison.

The skin care device may further comprise a haptic unit comprising a plurality of vibration modules spaced a preset distance from each other, wherein the controller calculates a skin area which needs care based on a locus of the relative locations with the skin areas, and the controller calculates a moving direction by comparing the calculated skin area which needs care with the relative location, and the controller controls corresponding one or more of the vibration modules to the calculated moving direction to generate vibration.

The skin care device further comprise a main body having a module coupling surface detachably coupled to the top tip head; a surface cap provided in the tip head and configured to contact with the module coupling surface of the main body; a recognition unit provided in the module coupling surface and comprising a plurality of terminals; and a pattern unit provided in the rear cap and electrically connected with one or more of the terminals provided in the recognition unit, wherein the controller is configured to recognize a signal value according to the arrangement of the one or more electrically connected terminals.

The skin care device may further comprise a memory in which a preset value for a care mode corresponding to the signal value is stored, wherein the controller is configured to select a care mode of the memory, corresponding to the recognized signal value, and determine whether to control the first electrode unit and the second electrode unit to apply a voltage and differentiate the intervals and intensity of the applied voltage.

The skin care device has following effects.

First of all, the skin care device is capable of providing care to the skin surface and the deep skin part simultaneously or selectively, using one device.

Furthermore, the skin care device is capable of enhancing the accuracy of the sensors.

Still further, the skin care device is capable of maximizing the design element.

Still further, the skin care device is capable of performing skin care to the uniform areas of the skin.

Still further, the skin care device is capable of minimizing the risk which might be caused by the skin care.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings, which are given by illustration only, and thus are not limitative of the present invention, and wherein.

DESCRIPTION OF SPECIFIC EMBODIMENTS

Devices for skin care may be realized through diverse methods. When a micro stimulation is applied to the human skin, activity of cell is changed enough to bring an effect of skin tightening and whitening and the like.

As typical examples of the skin care methods, there are a non-invasive method configured to apply electrical stimulation to the skin and an invasive method configured to apply a physical stimulation.

A conventional skin care device is not a hand-carry type. As wireless communication has developed and internal components have been small-sized, many diverse portable skin care devices are commonly used.

The non-invasive stimulation method configured to apply an electrical stimulation for skin care may include a high frequency band type for applying a high frequency band electrical stimulation and an optical type for applying visible ray area stimulation as main examples.

The high frequency band type skin care device may apply a 1 MHz high frequency stimulative energy to the human skin surface or the deep part of the skin.

However, the conventional skin care device is restricted only for deep skin care and it is not easy for a user to use a care for the skin surface and the deep part of the skin simultaneously or selectively.

To solve the disadvantage, the user is able to manage the skin by using a main device with diverse replaceable modules for various functions. However, no algorithm configured to automatically recognize the replaceable module is realized and the user has to set the module manually.

Meanwhile, the conventional skin care for business use is just small-sized and it is then insufficient to provide proper management for each user. For example, it is difficult to provide a corresponding feedback by recognizing a personal skin state. Even when there is a device capable of recognize the personal skin state, sensing accuracy can be deteriorated.

A new type of a skin care device is required which is capable of dataficating a personal skin state and skin care history and then providing a user's skin care based on the data.

Figure 1:
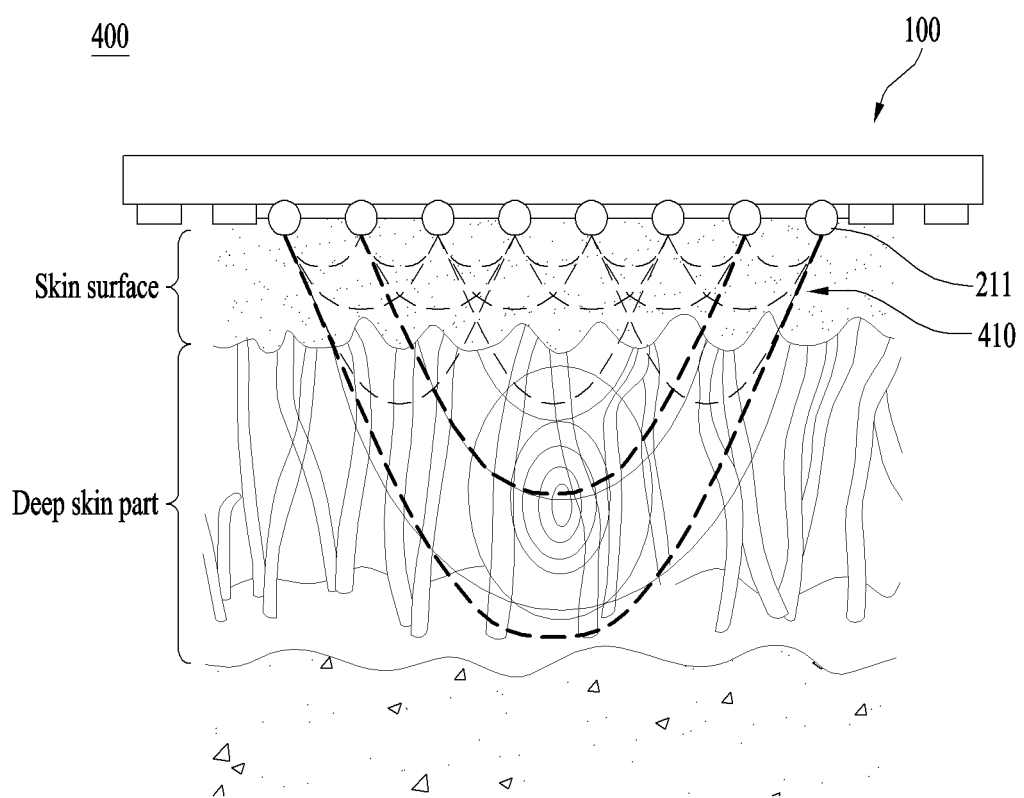
FIG. 1 is a schematic diagram to describe a skin care device in accordance with the present disclosure.

FIG. 1 is a schematic diagram to describe characteristics of a skin care device in accordance with the present disclosure configured to activate a skin surface and a deep part of a human skin 400.

The high frequency type includes at least two electrodes 211 configured to transmit a high frequency wave, in contact with the surface of the human skin 400, while one passage of the skin 400 connecting the electrodes with each other is employed as a conductor.

A specific one of the high frequency waves may be transmitted to the surface of the human skin 400 and another one to the deep part of the skin 400.

Diverse factors determine whether the high frequency wave 410 passes the skin surface or the deep part of the human skin 400.

Such diverse factors may include the range of the frequencies and the size and distance between the electrodes 211.

As the frequency gets lower 410, the degree of damping gets lower at a medium enough to reach a deep part of the skin 400. As the frequency gets higher, the degree of damping gets higher to apply stimulation within a lower part of the skin 400.

In addition, as they are larger, the electrodes 211 reach a deeper part of the skin enough to be applied to the deep skin part of the human skin 400. As they are spaced farther from each other, the electrodes 211 are more proper to be applied to the deep skin part of the human skin 400.

Figure 2:
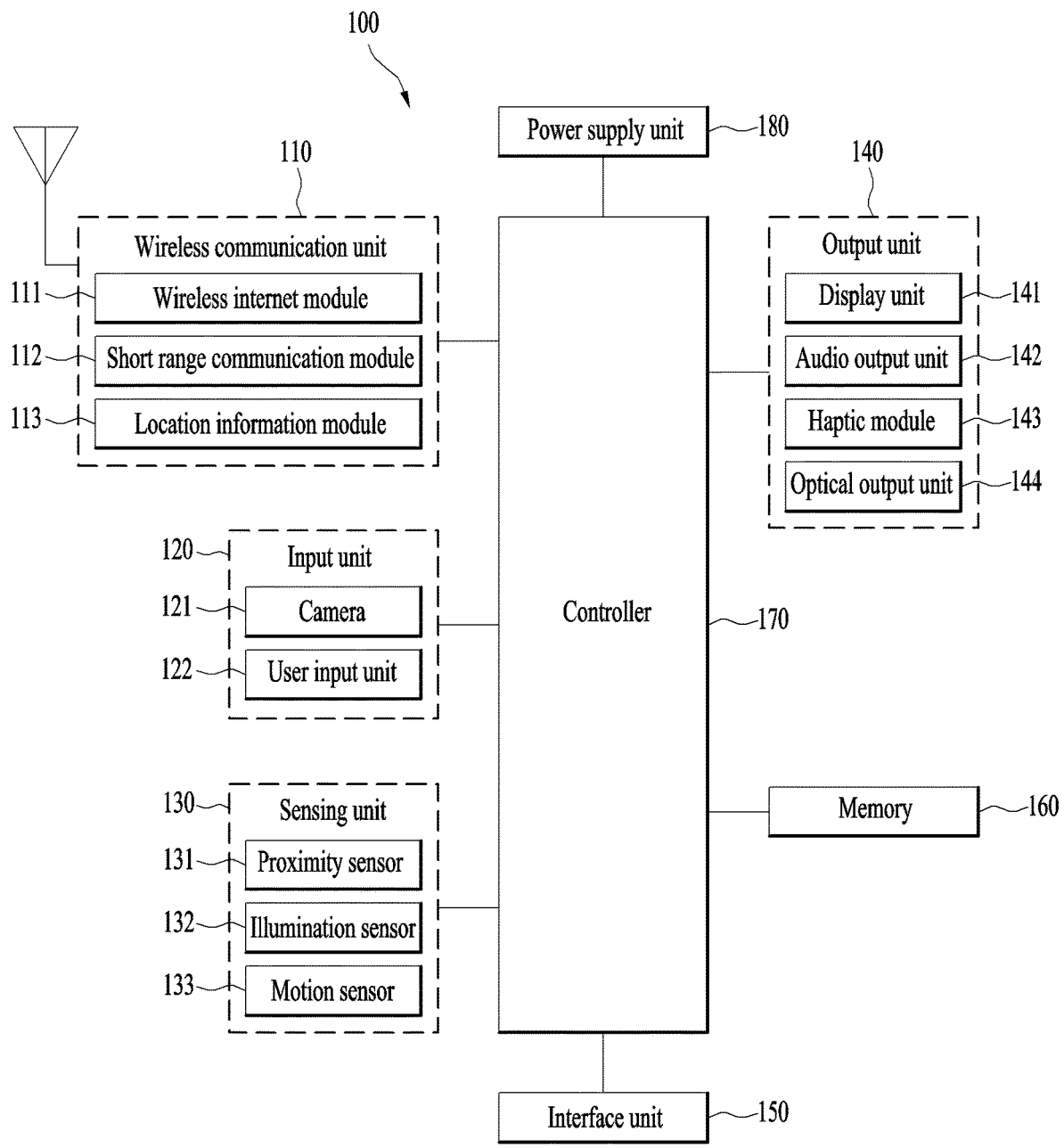
FIG. 2 is a block diagram to describe the skin care device.

FIG. 2 is a block diagram to describe the skin care device 100.

The skin care device 100 may include a wireless communication unit 110; an input unit 120; a sensing module 130; an output unit 140; an interface unit 150; a memory 160; a controller 170; and a power supply unit 180.

The elements shown in FIG. 1 are not necessarily provided to realize the skin care device 100 and the skin care device 100 explained through the description and the drawings may include more or less of the elements mentioned above.

More specifically, the wireless communication unit 110 out of the elements may include one or more modules configured to facilitate wireless communication between the skin care device 100 and a wireless communication system, between the skin care device 100 and another external terminal or between the skin care device 100 and an external server. The wireless communication unit 110 may include one or more modules configured to connect the skin care device 100 with one or more networks.

Such the wireless communication unit 110 may include one or more of a wireless internet module 111, a short range communication module 112 and a location information module 113.

The short range communication module 112 is configured to facilitate short-range communications. Suitable technologies for implementing such short-range communications include BLUETOOTH™, Radio Frequency Identification (RFID), Infrared Data Association (IrDA), Ultra-Wide Band (UWB), ZigBee, Near Field Communication (NFC), Wireless-Fidelity (Wi-Fi), Wi-Fi Direct, Wireless USB (Wireless Universal Serial Bus), and the like. The short-range communication module 112 in general supports wireless communications between the skin care device 100 and a wireless communication system, communications between the skin care device 100 and another skin care device 100, or communications between the skin care device and a network where another skin care device 100 (or an external server) is located, via wireless area networks. One example of the wireless area networks is a wireless personal area networks.

In some embodiments, another mobile terminal may be a wearable device, for example, a smart watch, a smart glass or a head mounted display (HMD), which is able to exchange data with the skin care device 100 (or otherwise cooperate with the skin care device 100). The short-range communication module 112 may sense or recognize the mobile terminal or wearable device, and permit communication between the mobile terminal or wearable device and the skin care device 100. In addition, when the sensed mobile terminal or wearable device is a device which is authenticated to communicate with the skin care device 100, the controller 170, for example, may cause transmission of data processed in the skin care device 100 to the wearable device via the short-range communication module 112. Hence, a user of the wearable device or mobile terminal may use the data processed in the skin care device 100 on the wearable device. Alternatively, the skin care device 100 is provided with the data processed in the mobile terminal or wearable device and then performs a specific motion or operation.

For example, the skin care device 100 transmits the measured data about a skin state to the mobile terminal or wearable device and figures out tendency of skin state change based on the database, so that it may feedback the data base to control the driving of the skin care device.

Short range communication techniques may be applied to the skin care device 100. Suitable short range techniques for the skin care device 100 include BLUETOOTH™, Radio Frequency Identification (RFID), Infrared Data Association (IrDA), Ultra-Wide Band (UWB), ZigBee, Near Field Communication (NFC), Wireless-Fidelity (Wi-Fi), Wi-Fi Direct, Wireless USB (Wireless Universal Serial Bus), and the like.

A NFC module provided in the skin care device 100 is configured to support non-contact short range wireless communication between terminals within a near field of 10 cm. The NFC module may be implemented a card mode, a reader mode or a P2P mode. To implement the NFC module in the card mode, the skin care device 100 may further include a security module for storing card information. The security module may be physical media such as Universal Integrated Circuit Card (UICC, for example, Subscriber Identification Module (SIM) or Universal SIM (USIM)), Secure Micro SD or a sticker or a logical media such as embedded Secure Element (SE). Data exchange based on SWP (Single Wire Protocol) may be performed between the NFC module and the securing module.

When the NFC module is implemented in the card mode, the skin care device 100 may transmit the card information stored like a conventional IC card to an external device.

When the NFC module is implemented in the reader mode, the skin care device may read data from an external tag. In this instance, the data received from the tag by the skin care device may be coded into NFC data exchange format determined in the NFC forum. The NFC forum regulates four record types. More specifically, the NFC forum regulates four RTD (Record Type Definition) Smart Poster, Text, URI (Uniform Resource Identifier) and General Control.

When the NFC module is implemented in the P2P (Peer-to-Peer) mode, the skin care device 100 is capable of performing P2P communication with other devices. At this time, LLCP (Logical Link Control Protocol) may be applied to the P2P communication. For the P2P communication, connection may be built between the skin care device 100 and other external terminal. The built connection may be categorized into a connectionless mode configured to exchange one packet and end; and a connection-oriented mode configured to exchange packets consistently. The P2P communication facilitates exchange of data, Bluetooth and a setup parameter for W-Fi connection. An available distance for the NFC communication is short so that the P2P mode can be effectively used in exchanging small data.

The location information module 113 is a module configured to acquire the location (or a current location) of the skin care device 100. Examples of the location information module 113 include a GPS (Global Positioning System) module and Wi-Fi (wireless Fidelity). For example, when using the GPS module, the user may acquire the location of the skin care device 100

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal. As one example, when the skin care device 100 uses a GPS module, a position of the skin care device 100 may be acquired by using a signal sent from a GPS satellite. As another example, when the skin care device 100 uses the Wi-Fi module, a position of the skin care device 100 can be acquired based on information related to a wireless access point (AP) which transmits or receives a wireless signal to or from the Wi-Fi module. If occasion occurs, the location information module 115 may perform one of the functions possessed by the other modules of the wireless communication unit 110 to gain data about the location of the skin care device 100 substitutionally or additionally. The location information module 115 is used so as to acquire the location (or current location of the skin care device 100, not limited to the module configured to directly calculate or acquire the location of the skin care device 100.

The input unit 120 may include a camera 121 or an image input unit; and a user input unit 112 for receiving the information input by the user, for example, a touch key, a mechanical key and the like. The image data collected by the input unit 120 is analyzed and processed into the user's control command.

The camera 121 includes one or more of a camera sensor (for example, CCD, CMS the like), a photo sensor (or image sensor) and a laser sensor.

The camera 121 and the laser sensor are combined with each other to sense touch of a sensing object for 3D. The photo sensor may be disposed on a display element and configured to scan movement of a sensing object near a touch screen. More specifically, the photo sensor has photo diodes and TR (Transistors) loaded in rows/columns and it is configured to scan the contents placed thereon, using an electrical signal which is variable according to the amount of light incident on a photo diode. The photo sensor is configured to calculate coordinates of a sensing object according to the change of light, so that the location information of the sensing object can be acquired.

The camera 121 provided in the skin care device 100 has a photographing function for a state of the skin surface. In case a display unit 141 is provided, the photographed skin surface is output for the user to check the skin surface.

The user input unit 122 is configured to receive input from the user. When information is input through the user input unit 122, the controller 170 is implemented to control the operation of the skin care device 100 based on the input information. Such the user input unit 122 may include mechanical input means (or a mechanical key, for example, a button, a dome switch, a jog wheel, a jog switch and the like); and touch input means. Examples of the touch input means include a virtual key displayed on a touch screen by software processing, a soft key and a visual key. Or the touch input unit may be a touch key arranged in the other area except the touch screen. Meanwhile, the virtual key or visual key may be displayed on the touch screen, in diverse types. For example, the diverse types include graphic, text, icons, video and combination of them.

The sensing unit 130 may include one or more sensors configured to sense one or more of peripheral information around and user information. For example, the sensing unit 130 may include a proximity sensor 131, an illumination sensor, a touch sensor, an acceleration sensor, a magnetic sensor, a G-sensor, a gyroscope sensor, a motion sensor 133, a RGB sensor, an IR (Infrared) sensor, a finger scan sensor, an ultrasonic sensor, an optical sensor (for example, a camera 121), a microphone, a battery gauge, an environment sensor (for example, a barometer, a hygrometer, a thermometer, a radioactivity detection sensor, a heat detection sensor, gas sensor and the like), a chemical sensor (for example, e-nose, a health care sensor, biometric sensor and the like. Meanwhile, the skin care device 100 described in the embodiments of the present disclosure may combine the information sensed by two or more of the sensors and utilize the combined information.

The sensing unit 130 is configured to sense one or more of the information stored in the skin care device 100, the environment information around the skin care device 100 and the user information, and to generate a corresponding sensing signal. The controller 170 is configured to control the drive or operation of the skin care device 100 based on the sensing signal or implement the data processing related with an application program installed in the skin care device 100 or functions or operations.

The proximity sensor 131 is a sensor configured to sense presence of an object approaching a predetermined detecting surface or existing nearby, using a force of an electromagnetic field or an infrared ray. The proximity sensor 131 may be arranged in an inner area of the skin care device 100 surrounded by the touch screen or near the touch screen.

Examples of the proximity sensor 131 include a transmission photo sensor, a direct reflection photo sensor, a high frequency oscillation proximity sensor, a capacitive proximity sensor, a magnetic proximity sensor and an infrared proximity sensor. When the touch screen is a capacitive touch screen, the proximity sensor 131 is configured to detect the approaching of the object based on change of the electric field caused by the proximity of the object with conductivity. In this instance, the touch screen (or touch sensor) itself may be categorized as the proximity sensor.

Meanwhile, for explanation sake, it may be defined as "proximity touch" that an object is located over near the touch screen, not in contact. It may be defined as "contact touch" that the object substantially contacts with the touch screen. The location where the object performs the proximity touch on the touch screen means the location of the object vertically corresponding to the touch screen. The proximity sensor 131 may be configured to sense a proximity touch and a proximity touch pattern (for example, a distance, direction, speed, time, location, moving state of proximity touch). Meanwhile, the controller 170 is configured to process corresponding data (or information) to the proximity touch and the proximity touch pattern sensed by the proximity sensor 131 and output corresponding visual information to the processed data on the touch screen. Moreover, the controller 170 may control the skin care device 100 to perform a different operation or process different data (or information) according as whether the touch for the same point on the touch screen is the proximity sensor or the contact touch.

The touch sensor is configured to sense the touch (or touch input) applied to the touch screen (or display unit 141), using at least one of diverse touch types including a resistive type, a capacitive type, an infrared type, an ultrasonic type and a magnetic field type.

As one example, the touch sensor may be configured to convert the pressure applied to a specific point of the touch screen or change of the capacity generated in a specific point into an electrical input signal. The touch sensor, for example, the touch objects may be a finger, a touch pen or a stylus pen and a pointer.

The controller 170 may perform a different or equal control according the kind of the touch object. It may be determined according to the current operation state of the skin care device 100 or the current application program which is being executed.

Meanwhile, the touch sensor and the proximity sensor mentioned above may independently or combiningly sense diverse types of touches such as a short (or tap) touch on the touch screen, a long touch, a multi touch, a drag touch, a flick touch, a pinch-in touch, a pint-out touch, a swype touch and a hovering touch.

The ultrasonic sensor is configured to recognize the location information about the sensing object, using an ultrasonic wave. Meanwhile, the controller 170 may calculate a location of a wave source based on the information sensed by an optical sensor and a plurality of ultrasonic sensors. The location of the wave generation source may be calculated by using a property that light is much faster than the ultrasonic wave, in other words, the time taken for the light to reach the optical sensor is faster than the time taken for the ultrasonic wave to reach the ultrasonic sensor. More specifically, a different between the time taken for the light as a reference signal to reach and the time taken for the ultrasonic wave to reach may be used in calculating the location of the wave generation source.

In case there is the touch input to the touch sensor, the corresponding signal(s) may be sent to a touch controller. The touch controller is implemented to process the signal(s) and transmit corresponding data to the controller 170. Accordingly, the controller 170 may figure out which area of the display unit 141 is touched. In this instance, the touch controller may be an independent element from the controller 170 or the controller 170 itself.

The output unit 140 may be configured to generate outputs which are related with the senses of sight, hearing and touch. The output unit 140 may include one or more of a display unit 141, an audio output unit 142, a haptic module 143 and an optical output unit 144. The display unit 141 may be configured of a multi-layer structure with the touch sensor or integrally formed with the touch sensor, so as to realize the touch screen. Such touch screen may function as the user input unit 122 which provides an input interface between the skin care device 100 and the user and an output interface between the skin care device 100 and the user.

The display unit 141 is configured to display (or output) the information processed in the skin care device 100. For example, the display unit 141 may display an execution screen of the application program driven in the skin care device 100 or GUI (Graphic User Interface) information according to such the execution screen information.

The interface unit 150 is employed as a passage with diverse external devices which are connected to the skin care device 100. The interface unit 150 may include one or more of a wire/wireless headset port, an external charger port, a wire/wireless data port, a memory card port and a port for connecting a device including an identification module. The proper control related with the connected external device may be performed in the skin care device 100, corresponding to the interface unit 150 to which the external device is connected.

The memory 160 is configured to store the data supporting diverse functions of the skin care device 100 therein. In the memory 160 may be stored a plurality of application programs or applications and data and commands for the operation of the skin care device 100. Some of the application programs may be provided in the skin care device 100 for basic functions from the release of the skin care device 100. Meanwhile, the application programs may be stored in the memory 160 and installed on the screen of the skin care device 100, so as to perform the operation (or functions) of the skin care device 100 based on the control of the controller 170.

The controller 170 is implemented to control not only the operations related with the application programs but also the common overall operation of the skin care device 100. The controller 170 may provide or process proper information to the user by processing the signal, data and information input or output via the components mentioned above.

The controller 170 may be the concept mixedly used with a controller 242 which will be described later.

The controller may control a predetermined number of the components mentioned above, referring to FIG. 1, so as to drive the application programs stored in the memory 160.

Moreover, the controller 170 may combine and operate two of more of the components provided in the skin care device 100.\

The power supply unit 180 is provided with an external power source and an internal power source and configured to supply the electric power to each of the components provided in the skin care device 100. Such the power supply unit 180 includes a battery and the battery may be a built-in battery or replaceable battery.

A predetermined number of the components may cooperate with each other to realize the operation, control or control method of the skin care device 100. Also, the operation, control or control method of the skin care device 100 may be realized on the screen of the skin care device by the driving of at least one application program stored in the memory 160.

Figure 3:
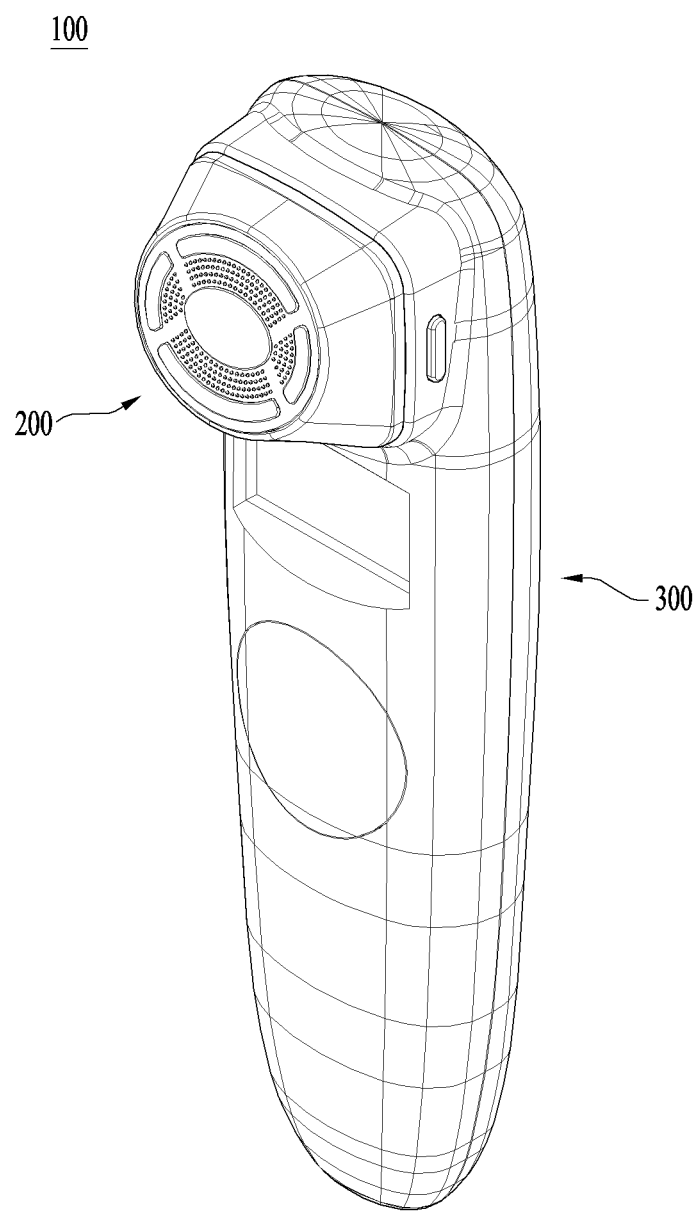
FIG. 3 is a front perspective diagram of the skin care device.
Figure 4:
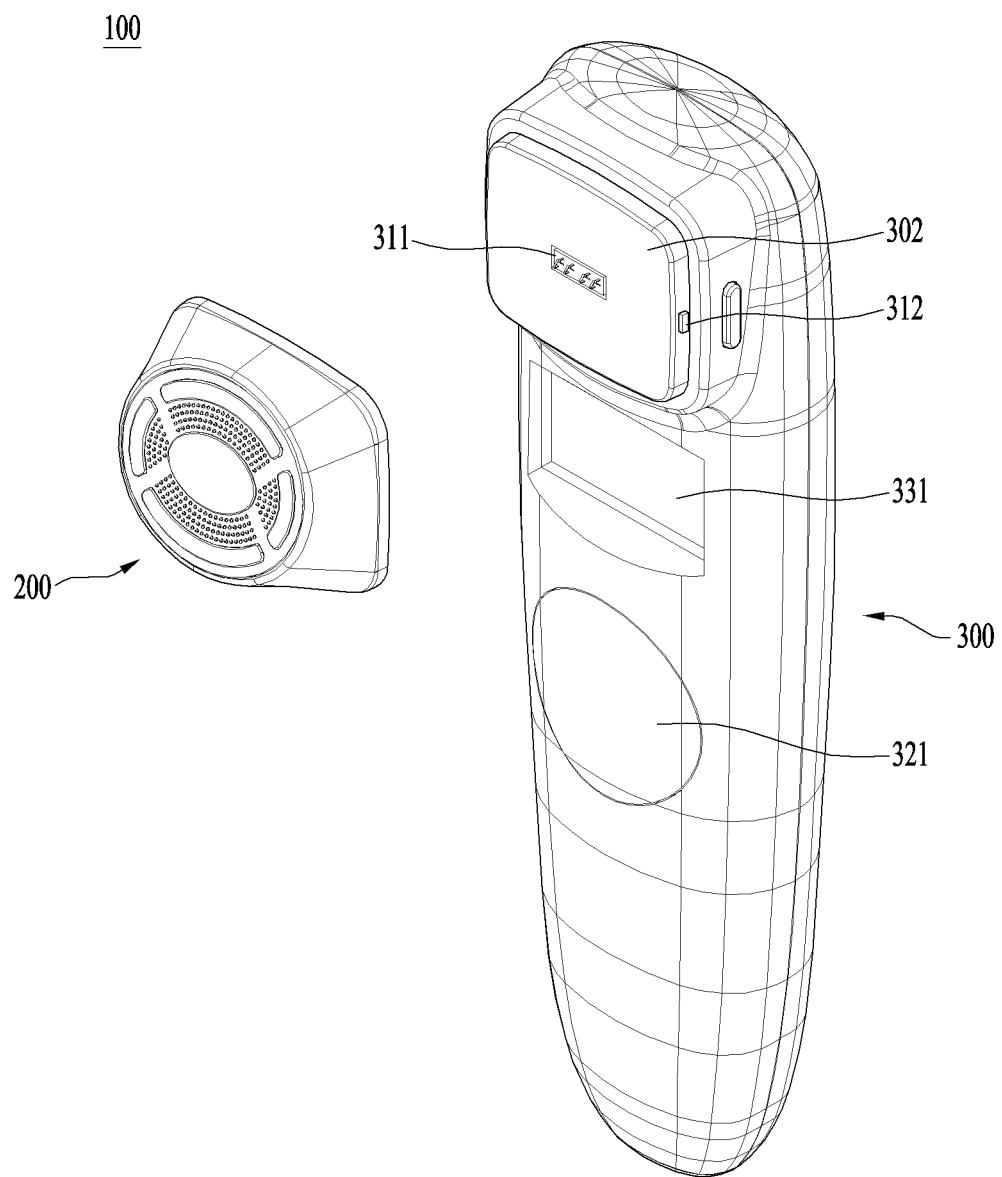
FIG. 4 is a front perspective diagram illustrating a state where a tip head of the skin care device is demounted.

FIG. 3 is a front perspective diagram of the skin care device 100 and FIG. 4 is a front perspective diagram illustrating a state where a tip head 200 of the skin care device 100 is demounted.

The skin care device 100 may include a tip head 200 and a main body 300. While holding the main body 300, the user may put the tip head 200 on the user's skin and perform high-frequency care.

As occasion occurs, the tip head 200 may be provided as a different type according to the user's intended use.

The tip head 200 may be detachably coupled to the main body 300. The coupling between the two may be detachable for mutual attraction by a magnetic force or by using a hook 312. In case of using the hook 312, a push button may be provided to facilitate the decoupling of the tip head from the main body.

Figure 5:
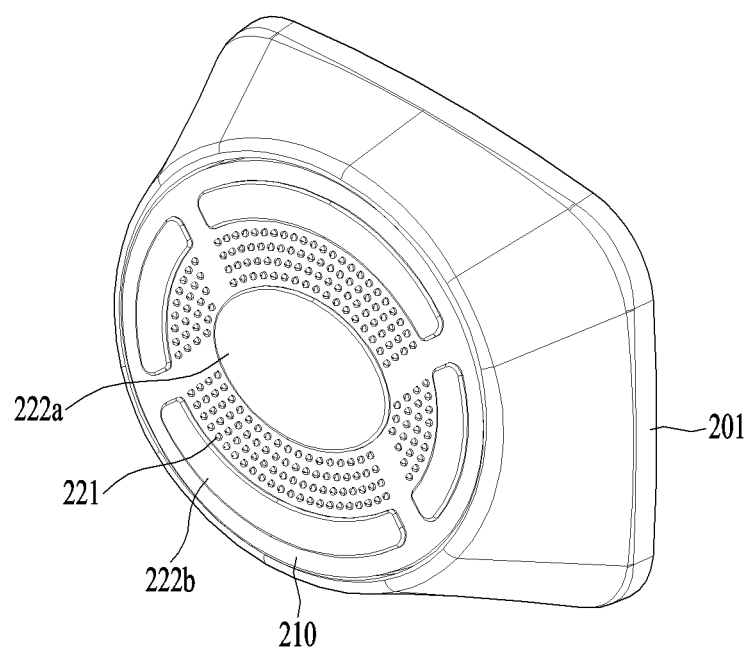
FIG. 5 is a diagram illustrating one embodiment of the tip head provided in the skin care device.
Figure 6:
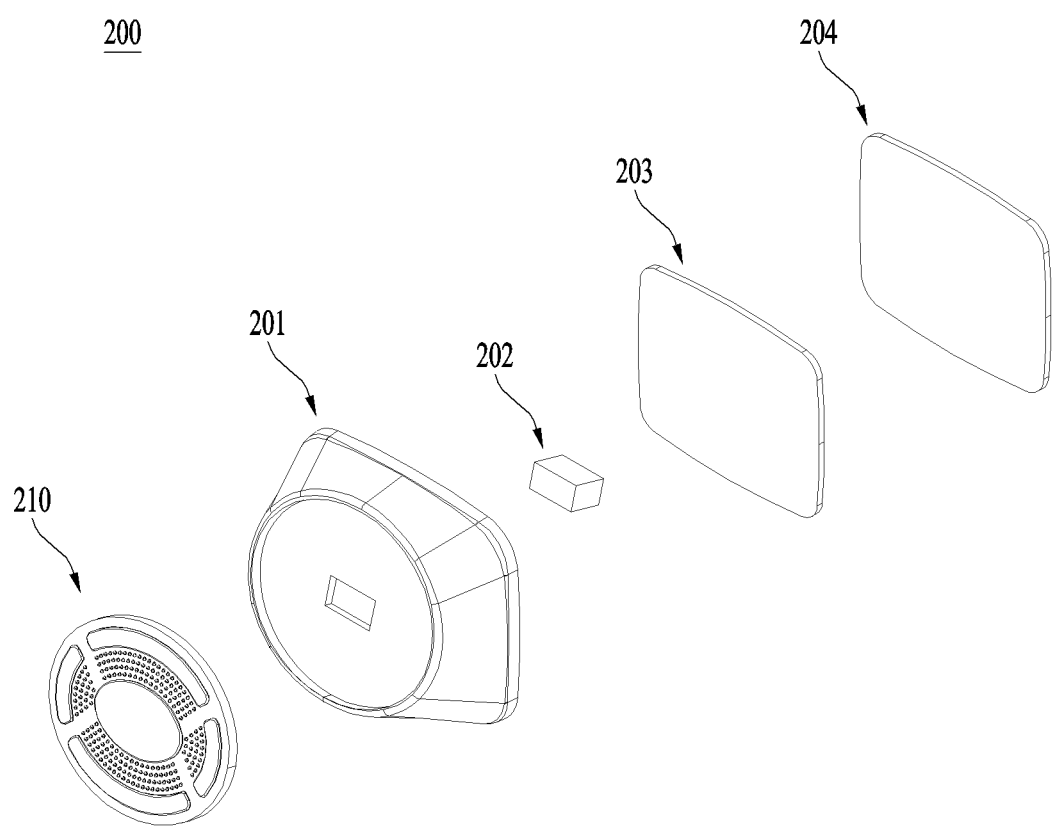
FIG. 6 is an exploded perspective diagram illustrating one embodiment of the tip head provided in the skin care device.

FIG. 5 is a diagram illustrating one embodiment of the tip head 200 provided in the skin care device 100.

As one example of the replaceable module may be provided a surface-deep part combined use module 200a configured to apply high frequency stimulation to the surface and the deep part of the skin simultaneously.

A front surface of the tip head 200 may be circular-shaped and an electrode unit 211 provided in the tip head 200 may be arranged in a corresponding shape to the circular front surface.

The electrode unit 211 may include a first electrode unit 221 for forming a high frequency to simulate the skin surface and a second electrode unit 222 for forming a high frequency to stimulate the deep part of the skin.

A controller 242 may control to apply a high frequency voltage to the first electrode unit 221 and the second electrode unit 222. The first and second electrode units 221 and 222 may be independently driven based on the control of the controller 242. In other words, the first electrode unit 221 or the second electrode unit 222 may be driven independently or they may be driven simultaneously as occasion occurs.\

The second electrode unit 222 may be dividedly provided in a center and an outer area of the front surface of the tip head 200 to be arranged in both sides of the first electrode unit 221. For convenience sake, the electrode 211 provided in the center may be defined as the inner electrode 222a and the electrode 211 provided in the outer area as the outer electrode 222b.

The inner electrode 222a may be a positive electrode 211 and the outer electrode 222b may be a negative electrode 211 or vice versa.

The positive electrode 211 and the negative electrode 211 may be configured to contact with the skin surface, while being electrically connected with each other to generate a high frequency wave.

Even when the outer electrode 222b is provided as a plurality of segmented electrodes, the segmented outer electrode 222b has the same electrode 211 and the inner electrode 222a and the outer electrode 222b have the opposite electrodes, respectively. The outer electrode 222b is spaced the maximum distance apart from the inner electrode 222a so as to deliver the high frequency stimulation even to the deep part of the skin effectively.\

According to the principle of the high frequency wave, approximately a half of the distance between the positive electrode 211 and the negative electrode 211 may be the high frequency application depth.

The first electrode unit 221 may be provided between the second electrode units separated from the front surface of the tip head 200. In other words, the first electrode unit 221 may form a donut shape.

The first electrode unit 221 also includes one or more of the positive electrode 211 and negative electrode 211.

The electrodes 211 of the first electrode unit 221 may be aligned in an array and each neighboring electrodes 211 opposite to each other are paired and arranged alternatively.

When the opposite electrodes 211 are alternatively arranged, the neighboring opposite electrodes 211 may form the minimum distance so as to supply the high frequency stimulation even to the thinnest point on the skin surface.

Even not-neighboring opposite electrodes 211 as well as the neighboring opposite electrodes 211 may form the high frequency waves to apply the stimulation to a deeper part of the skin.

In other words, the plurality of the electrodes 211 provided in the first electrode unit 221 may be configured to generate high frequency waves combinedly to transmit the stimulation to various parts of the skin to various depths.

Each electrode 211 of the first electrode unit may have a uniform shape and a uniform area in contact with the skin, so that the electrodes having the same shapes and areas can transmit the uniform stimulation to the area in contact with the skin.

According to the principle, the distance between each two neighboring electrodes 211 of the first electrode unit 221 may be a first distance or less and the distance between each neighboring or not-neighboring electrodes 211 may be a second distance or more.

The depth of the skin stimulation applied by the high frequency wave may be variable according to the distance between the electrodes 211 and the area of the electrodes 211 configured to contact with the skin. The larger is the area of the electrodes contacting with the skin, the deeper part of the skin the stimulation is applied.

Accordingly, the skin contact area of each electrode 211 provided in the second electrode unit 222 may be a second area or more, while the skin contact area of each electrode 211 provided in the first electrode unit 221 may be a first area or less.

The distance and skin contact area between the electrodes 211 mentioned above may determine the depth of the skin stimulation.

In addition, the factors may affect the frequency value of the high frequency wave. To simplify the circuit, it is preferred that the same frequency is applied to the first electrode unit 221 and the second electrode unit 222. The applied frequency value may be 1 MHz.

Accordingly, the depth of the skin stimulation may be variable according to the distance between the electrodes, the skin contact area of the electrode 211 and the applied frequency value.

The arrangement shown in FIG. 5 is one example and other examples may be provided based on the factors.

The first electrode unit 221 may have the pin-electrodes 211 aligned in the array. In this instance, the mutual activation of the neighboring electrodes 211 may be applied to a wide skin area simultaneously. The electrodes may form diverse distances with not-neighboring free electrodes 211 so as to apply the electrical stimulation to skin parts with various depths.

The first electrode unit 221 and the second electrode unit 222 may include a metallic material with conductivity. Examples of the metallic material may include gold (Au) or copper (Cu).

Figure 7:
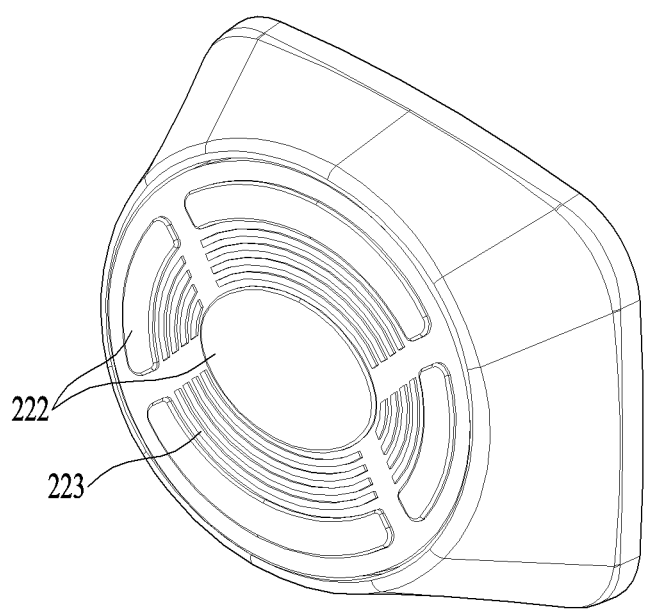
FIG. 7 is a diagram illustrating another embodiment of the tip head provided in the skin care device.

FIG. 7 is a diagram illustrating another embodiment of the tip head 200 provided in the skin care device. 100

A front cap 210 may have the first electrode unit 221 and the second electrode unit 222 mounted therein. The front cap 210 may be provided as a PCB (Printed Circuit Board) for forming an electrical circuit through a pattern process for printing a pattern on a non-conductive substrate 203 or a mounting process for mounting a conductive member on the substrate 203. The conductive member may include a first electrode unit 221 and a second electrode unit 222.

The front cap 210 including the first and second electrode units 221 and 222 may be coupled to a head housing 201.

The head housing 201 is configured to facilitate easy contact of the front cap 210 including the first and second electrode units 221 and 222 projected from the skin care device 100 with the skin and form an electric control unit for mounting electronic components including the substrate 203 therein.

The substrate 203 may form an electrical circuit for applying a voltage to the first and second electrode units 221 and 222.

A connector 202 may be configured to electrically connect the substrate 203 with the front cap 210.

A rear cap 204 may define a rear surface of the tip head 200. The rear cap 204 may include a magnetic material for detachably coupling to the main body 300.

FIG. 7 is a diagram illustrating another embodiment of the tip head 200 provided in the skin care device 100.

As another embodiment of the tip head 200 coupled to the skin care device 100 to perform preset functions, a deep-skin-part module 200b is disclosed and the deep-skin-part module 200a is configured to perform only deep skin part care, not double care for the skin surface and the deep skin part simultaneously.

A first electrode unit 221 provided in the skin surface-deep skin part may be replaced by a third electrode unit 223.

The third electrode unit 223 may be arranged in the same position to the first electrode unit 221 but it has a linear pattern, not a dot-pattern.

In other words, electrodes 211 of the third electrode unit 223 have a relatively large area, compared with the electrodes 211 of the first electrode unit 211.

Accordingly, the third electrode unit 223 may facilitate high frequency care for the deep skin part, not the skin surface.

The third electrode unit 223 may include a plurality of electrodes 211 disposed in a multi-layer shape.

A lateral area of the multi-layer may be exposed to the skin contact surface.

Figure 8:
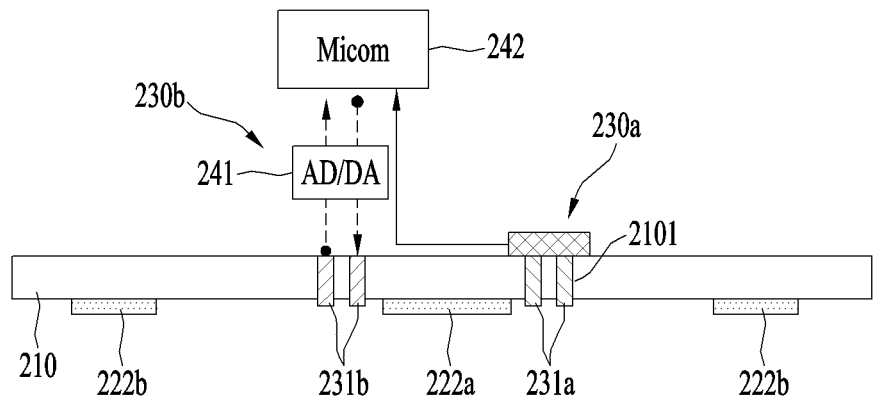
FIG. 8 is a sectional diagram schematically illustrating the tip head.

FIG. 8 is a sectional diagram schematically illustrating the tip head. 200

The sensing unit 230 may include a temperature sensor 230a configured to measure the skin temperature; and a moisture sensor configured to figure out a moisturized state of the skin.

As one typical example of the moisture sensor, a BIA (Bioelectric Impedance Analysis) sensor may be provided. The BIA sensor 230B may be configured to measure body water and a fat amount by measuring a resistance value.

The other components of the sensing unit 230 may be provided in the replaceable type module tip head 200, except a sensor probe 231.

In other words, only the sensor probe 231 of the sensing unit 230 may be provided outside the front cap 210 via through hole 2101 of the front cap 210.

As the other components of the sensing unit 230 are provided in the tip head 200, except the sensor probe 231, the user's feeling of irritation and the measurement error generated by external noise may be minimized.

The sensor probe 231 may be provided between the inner electrode 222a and the outer electrode 222b of the second electrode unit 222, to directly contact with the user's skin.

Especially, in case of using the temperature sensor 230a, the most heat is generated in an area near the inner electrode 222a of the combined replaceable module in accordance with the embodiment. Considering the safety stability, it is necessary for the probe 231 of the temperature sensor 230 to measure the largest heat generation point and the temperature sensor 230a may be provided in the largest heat generation point.

The temperature sensor probe 231a may be formed of metal so as to transmit the temperature of the skin surface to the temperature sensor 230a. The BIA sensor probe 231B may be formed of metal so as to transmit a resistance state of the skin surface to the moisture sensor.

Examples of the temperature sensor probe 231a or the BIA sensor probe 231A may include gold (Au) and copper (Cu).

Based on the reasons mentioned above, the sensor probe 231 of the sensing unit 230 may replace one or more electrodes 211 of the array provided in the first electrode unit 221. In other words, the array electrode 221 of the first electrode unit 221 and the sensor probe 231 may have the same terminal, except the circuit configuration.

In this instance, the design improvement effect may be expected.

The BIA sensor 230B may be configured to transmit a signal to the controller 242 via a converter 242. The controller 242 may be implemented to perform the control related with the skin care based on the skin temperature measured by the temperature sensor 230a and the skin resistance measured by the BIA sensor 230B. In other words, the controller 242 may control whether to apply a voltage to the first electrode unit 221 and the second electrode unit 222 and the period and intensity of the applied voltage.

The controller 242 may mean the concept including a memory device of a microprocessor having a calculation process unit and interface circuit.

Figure 9:
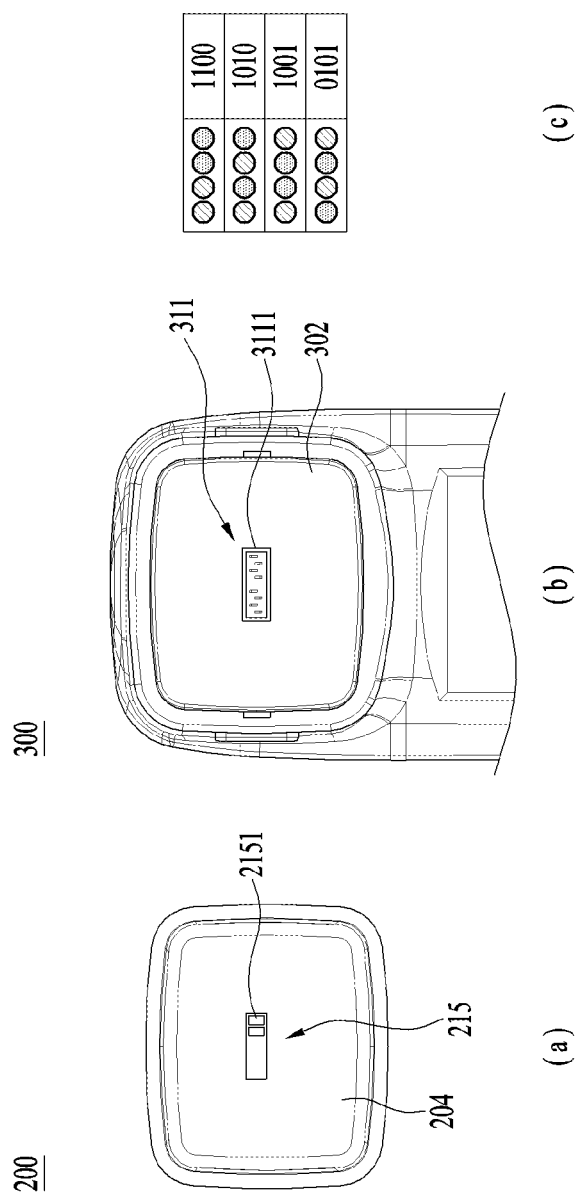
FIG. 9 is a conceptual diagram illustrating a coupling surface between the tip head and a main body and a signal pattern of a recognition unit.

FIG. 9 is a conceptual diagram illustrating a coupling surface between the tip head 200 and the main body 300 and a signal pattern of a recognition unit 311.

FIG. 9(a) illustrates an area of the rear cap 204 provided in the tip head 200 and FIG. 9(b) illustrates a module coupling surface 302 of the main body 300. FIG. 9(c) illustrates examples of the signal value recognized by the recognition unit 311.

As mentioned above, the tip head 200 of the skin care device 100 may be provided as the replaceable module type.

The replaceable module may be an invasive type module having a micro-needle although not shown as well as the skin surface-skin deep part combined module 200a or the deep skin part module 200b mentioned above.

The invasive type module may include a structure configured to supply an element for generating a specific effect to the skin.

The user may couple a proper tip head 200 for use to the main body 300.

A pattern unit 215 and a recognition unit 311 may be provided for the skin care device 100 to recognize which one is coupled out of the diverse tip heads 200.

The recognition unit 311 may be provided in a module coupling surface 302 of the main body 300 to the tip head 200. The recognition unit 311 may include a plurality of terminals.

The pattern unit 215 may be provided in the tip head 200 and electrically connected with the plurality of the terminals 3111 provided in the recognition unit 311.

The recognition unit 311 and the pattern unit 215 may be directly connected with the electrodes 211 configured to perform the command based on the voltage signal applied by the controller 242 or auxiliary electrodes 211 may be provided to perform the recognition.

The controller 242 may be configured to recognize the type of the tip head 200 based on the type of the pattern unit 215 coupled to the recognition unit 311.

When a pattern of a paternal unit terminal 2151 connected with a pattern unit terminal 2151 of the recognition unit 311 is corresponding to a preset pattern, the controller 242 may recognize that the connected module is a preset type module.

For example, it is assumed that there are four terminals 3111 of the recognition unit 311. A pattern unit terminal 2151 of the skin surface-deep skin part combined module 200a may be electrically connected with the first and second terminals 3111 of the recognition unit 311. The controller 242 recognizes that as 1100 and that the skin surface-deep skin part combined module 200a is coupled, corresponding to a preset pattern stored in the memory (160, see FIG. 1).

The embodiment is not limited thereto and the coupled replaceable module type may be recognized by corresponding the diverse examples.

Meanwhile, the recognition unit 311 and the pattern unit 215 are not only the structure for simply recognizing the tip head but also the passage for supplying currents for driving the skin care.

The recognition unit 311 and the pattern unit terminal 2151 may use a different resistance element or a different capacitance element. Alternatively, the wiring may be differentiated to recognize the cut or connection of the circuit.

Referring to FIG. 4 again, the user input unit 321 may be provided in the main body 300.

An automatic conversion key may be configured to allow the user to select a care mode, when a deep skin part care and a skin surface care are selectable by the user. For example, when the key is pressed one time, only the deep skin part care is performed. When the key is pressed one more, only the skin surface care is performed. When the key is pressed three times serially, the deep skin part care and the skin surface care are performed simultaneously by applying voltages to the first electrode unit 221 or the second electrode unit 222.

In case of performing only the deep skin part care or the skin surface care, unnecessary care is omitted and the power consumption is minimized, compared with the case of performing the simultaneous care for the skin surface and the deep skin part.

An interval select key is configured for the user to select an interval of the applied voltage. When the interval select key is pressed once, a voltage is applied consistently. When the key is pressed one more, the voltage is applied at intervals of several seconds. When the key is pressed one more, in other words, three times serially, the voltage is applied at intervals of several minutes.

Such the voltage application intervals may be preset by the user's selection and the coupled module.

When the voltage applying intervals proper to the deep skin part or skin surface care is different from the voltage applying intervals proper to the intensive deep skin part care, the controller 242 may control the power supply unit to supply the power, corresponding to the preset intervals.

The applied voltage may be preset to be differently applied according to the type of the coupled care module.

The main body 300 may include a haptic unit for generating vibration and a display unit 331 for outputting an image, as the output unit. The haptic unit may include a vibration module for generating vibration.

The skin care device 100 may perform diverse alarm functions by using the output unit.

For example, the user may be warned when the skin care device 100 is not moving for a preset time period during the driving.

At this time, so as to sense whether the skin care device 100 is moving, the main body 300 may include a motion sensor (133, see FIG. 1) such as a gyro-sensor or an acceleration sensor to sense the location or variation of the location or direction.

Such warning may be realized by the haptic unit 341 or the display unit 331 mentioned above or an alarm sound may be output via a speaker.

The user is notified that the skin is likely to be damaged by the continuous stimulation applied to a specific point of the skin indirectly by the warning alarm which requires the user's moving the skin care device, so that he or she can move the location of the skin care device 100.

Figure 10:
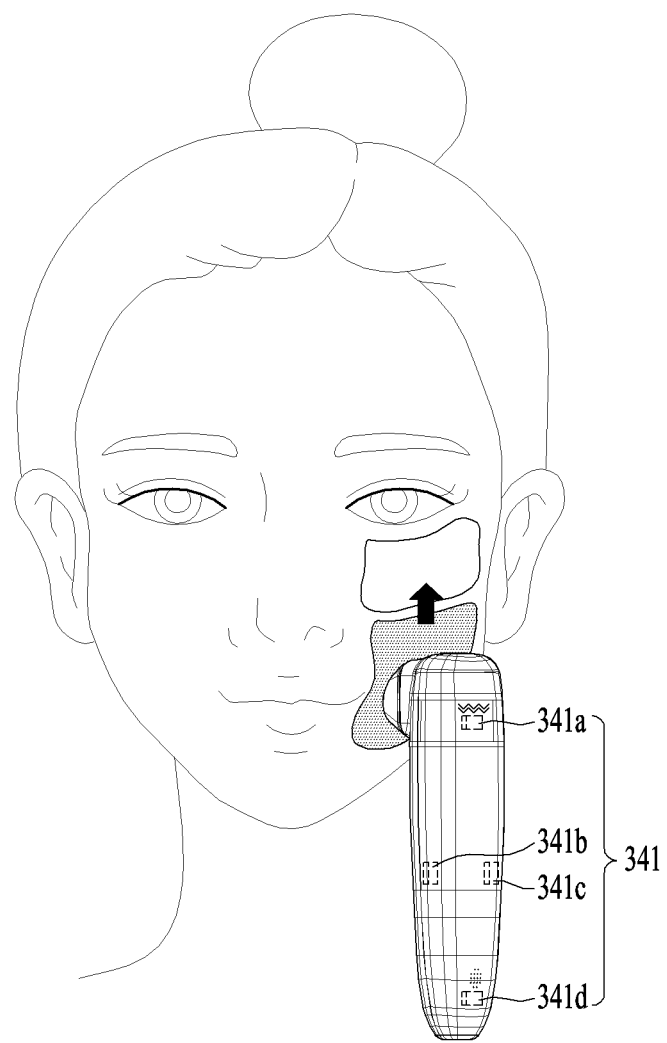
FIG. 10 is a diagram illustrating one embodiment of the skin care device.

FIG. 10 is a diagram illustrating one embodiment of the skin care device 100.

The haptic unit 341 may include a plurality of vibration modules 3411. The vibration module 3411 means the unit configured to generate vibration independently. When the plurality of the vibration modules 3411 are spaced a preset distance part within the main body 300, the controller 242 may independently drive the vibration modules 3411 to generate various combinations of vibration patterns which can be distinguished by the user.

The haptic unit 341 including the plurality of the vibration module 3411 may be used in generating an alarm for inducing a travelling direction of the care.

For example, the vibration modules 3411 are provided in four points in all directions of the skin care device 100 and the controller 242 controls the vibration module 3411 to generate vibration corresponding to an intended direction, so that the user can be induced to move the skin care device 100 toward the intended direction. As well as the haptic unit 341, the display is controlled to display a skin area which needs more care on the display visually.

The algorithm for calculating the movement inducing direction may be realized by the motion sensor (133, see FIG. 1) and the temperature sensor 230*a*.

For example, the user is induced to start to use the skin care device 100 at one point of the face skin. The movement of the motion sensor is activated from the moment when the user contacts the skin care device 100 with the skin surface and it is approximately calculated whether the skin care device 100 is moved around all of the desired area of the face skin surface.

Alternatively, a relative location to the skin area is calculated and it is then calculated based on the calculated relative location whether skin care is performed over all of the desired skin area. The detailed algorithm will be described later.

Figure 11:
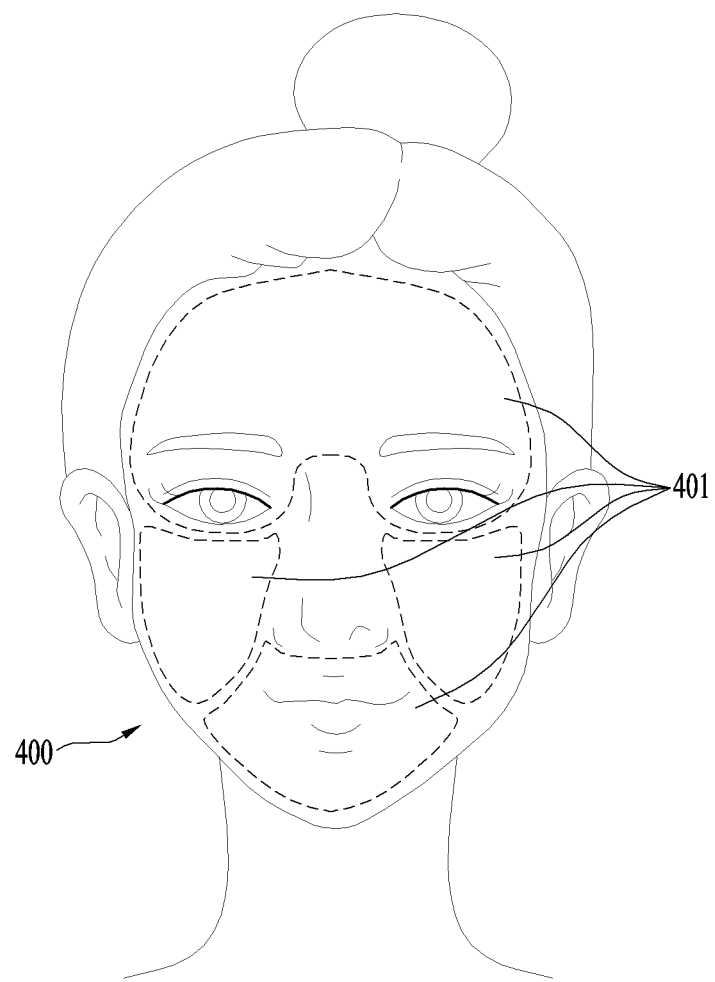
FIG. 11 is a diagram schematically illustrating a temperature distribution area according to a skin area.

FIG. 11 is a diagram schematically illustrating a temperature distribution area according to a skin area.

Temperature distribution data for the skin area 401 may be used in figuring out a relative location with respect to a skin area of the skin care device 100, especially, the face skin area.

The skin temperature distribution commonly shows a different relative distribution for each skin area 401. Accordingly, such the temperature distribution data is compared with the measured temperature and the location of the skin care device 100 may be figured out based on the result of the comparison.

The temperature distribution data for the skin area, especially, the face skin area 401 may be pre-stored in the memory (160, see FIG. 1). The temperature distribution data according to the skin area 401 may be generated by the user interface preset at the first use of the skin care device.

Alternatively, the temperature distribution is simply divided into a preset number of ranges and data about the temperature distribution area 401 may be formed, corresponding to each of the ranges. Each boundary shape of the temperature distribution areas 401 may be a comparison reference.

The controller 242 is configured to make data about the skin temperature change according to the location and direction change of the skin care device 100 sensed by the motion sensor and the location and direction change sensed by the temperature sensor 230*a*. Hence, the controller 242 compares the data with the stored temperature distribution data and determines the current location of the skin care device 100 based on the result of the comparison.

The controller 242 calculates the skin area which needs care based on a locus of relative locations on the skin area and compares the calculated skin area with a relative location to the calculated skin area to calculate a moving direction.

Corresponding ones of the vibration modules to the calculated moving direction are controlled to generate vibration.

Various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A skin care device comprising:
a main body;
a tip head projected from the main body;
a front cap defining a front surface of the tip head;
a first electrode unit comprising a plurality of pin-electrodes aligned in an array in the front surface of the front cap;
a second electrode unit comprising a positive electrode and a negative electrode which are dividedly aligned on both sides of the first electrode unit; and
a controller to control a high frequency voltage to be independently applied to the first electrode unit and the second electrode unit,
wherein a skin contact area of the second electrode unit is larger than a skin contact area of the first electrode unit.

2. The skin care device of claim 1, wherein the first electrode unit array is donut-shaped, and
wherein the positive electrode and the negative electrode of the second electrode unit are divided into an inner area and an outer area of the donut shape.

3. The skin care device of claim 2, further comprising:
a sensing unit provided in the tip head to expose a sensor probe to the front surface of the front cap via the front cap.

4. The skin care device of claim 3, wherein the sensor probe is provided in an area between the positive electrode and the negative electrode of the second electrode unit.

5. The skin care device of claim 4, wherein the sensor probe is provided instead of one or more of the terminals provided in the array of the first electrode unit.

6. The skin care device of claim 3, wherein the sensing unit comprises a temperature sensor to measure skin temperature and a moisture sensor to measure skin moisture, and
wherein the controller determines whether to apply a voltage and differentiate the intervals and intensity of the applied voltage based on a temperature value measured by the temperature sensor and a moisture value measured by the moisture sensor.

7. The skin care device of claim 1, further comprising:
a temperature sensor to measure skin temperature;
a memory in which temperature distribution data according to skin areas is stored; and
a motion sensor to sense location or direction change of the skin care device,
wherein the controller compares the skin temperature change according to the sensed location and direction change with the temperature distribution data and determines a relative location within a skin area based on the result of the comparison.

8. The skin care device of claim 7, further comprising:
a haptic unit comprising a plurality of vibration modules spaced a preset distance from each other,
wherein the controller calculates a skin area which needs care based on a locus of the relative locations within the skin areas,
wherein the controller calculates a moving direction by comparing the calculated skin area which needs care with the relative location, and
wherein the controller controls corresponding one or more of the vibration modules in the calculated moving direction to generate vibration.

9. The skin care device of claim 1, further comprising:
a module coupling surface detachably coupled to a top of the tip head;
a surface cap provided in the tip head to contact with the module coupling surface;
a recognition unit provided in the module coupling surface and comprising a plurality of terminals; and
a pattern unit provided in a rear cap of the tip head and electrically connected with one or more of the terminals provided in the recognition unit,
wherein the controller recognizes a signal value according to the arrangement of the one or more electrically connected terminals.

10. The skin care device of claim 9, further comprising:
a memory in which a preset value for a care mode corresponding to the signal value is stored,
wherein the controller selects a care mode of the memory, corresponding to the recognized signal value, and determines whether to control the first electrode unit and the second electrode unit to apply a voltage and differentiate the intervals and intensity of the applied voltage.

* * * * *